United States Patent [19]

Brown et al.

[11] Patent Number: 5,123,528
[45] Date of Patent: Jun. 23, 1992

[54] PACKAGE FOR NEEDLE SUTURES OR THE LIKE

[75] Inventors: David L. Brown, Wallingford; Henry A. Holzwarth, Weston; Craig W. Leary, Bridgeport, all of Conn.

[73] Assignee: United States Surgical Corporation, Norwalk, Conn.

[21] Appl. No.: 638,384

[22] Filed: Jan. 7, 1991

[51] Int. Cl.$^5$ .............................................. A61B 17/06
[52] U.S. Cl. ...................... 206/63.3; 53/432; 53/473
[58] Field of Search ................. 206/63.3, 227; 53/432, 53/473

[56] References Cited

U.S. PATENT DOCUMENTS

| | | | |
|---|---|---|---|
| D. 263,505 | 3/1982 | Black | 206/63.3 X |
| D. 272,600 | 2/1984 | Kubas | 206/63.3 X |
| 3,136,418 | 6/1964 | Stacy et al. | 206/63.3 |
| 3,162,307 | 12/1964 | Regan, Jr. | 206/63.3 |
| 3,206,018 | 9/1965 | Lewis et al. | 206/63.3 |
| 3,280,971 | 10/1966 | Regan, Jr. | 206/63.3 |
| 3,338,019 | 8/1967 | Trewella et al. | |
| 3,338,401 | 8/1967 | Regan, Jr. | 206/63.3 |
| 3,363,751 | 1/1968 | Shave et al. | |
| 3,444,994 | 5/1969 | Kaepernik et al. | 206/63.3 |
| 3,487,917 | 1/1970 | Shave et al. | |
| 3,490,192 | 1/1970 | Regan, Jr. | |
| 3,545,608 | 12/1970 | Berger | 206/63.3 |
| 3,613,879 | 10/1971 | Kemble | 206/63.3 |
| 3,627,120 | 12/1971 | Bordeau | 206/63.3 |
| 3,759,376 | 9/1973 | Lisowski | 206/63.3 |
| 3,779,375 | 12/1973 | Foster | 206/63.3 |
| 3,857,484 | 12/1974 | Thyen | 206/63.3 X |
| 3,939,969 | 2/1976 | Miller et al. | 206/63.3 |
| 3,972,418 | 8/1976 | Schuler et al. | 206/63.3 |
| 3,985,227 | 10/1976 | Thyen et al. | 206/63.3 |
| 4,034,850 | 7/1977 | Mandel et al. | 206/63.3 |
| 4,063,638 | 12/1977 | Marwood | 206/63.3 |
| 4,089,409 | 5/1978 | Cerwin | 206/63.3 |
| 4,120,395 | 10/1978 | Mandel et al. | 206/63.3 |
| 4,126,221 | 11/1978 | Cerwin | 206/63.3 |
| 4,135,623 | 1/1979 | Thyen | 206/63.3 |
| 4,183,431 | 1/1980 | Schmidt et al. | 206/63.3 |
| 4,249,656 | 2/1981 | Cerwin et al. | 206/63.3 |
| 4,253,563 | 3/1981 | Komarnycky | 206/63.3 |
| 4,284,194 | 8/1981 | Flatau | 206/63.3 |
| 4,369,880 | 1/1983 | Giggey et al. | 206/63.3 |
| 4,391,365 | 7/1983 | Batchelor | 206/63.3 |
| 4,406,363 | 9/1983 | Aday | 206/63.3 |
| 4,412,613 | 11/1983 | Kubas | 206/63.3 |
| 4,412,614 | 11/1983 | Ivanov et al. | 206/63.3 |
| 4,424,898 | 1/1984 | Thyen et al. | 206/63.3 |
| 4,427,109 | 1/1984 | Roshdy | 206/63.3 |
| 4,496,045 | 1/1985 | Ferguson et al. | 206/63.3 |
| 4,533,041 | 8/1985 | Aday et al. | 206/63.3 |
| 4,549,649 | 10/1985 | Roshdy | 206/63.3 |
| 4,555,016 | 11/1985 | Aday et al. | 206/63.3 |
| 4,572,363 | 2/1986 | Alpern | 206/63.3 |
| 4,573,575 | 3/1986 | Bergrath et al. | 206/380 |
| 4,574,948 | 3/1986 | Huck et al. | 206/63.3 |
| 4,574,957 | 3/1986 | Stead | 206/63.3 |
| 4,615,435 | 10/1986 | Alpern et al. | 206/63.3 |
| 4,699,271 | 10/1987 | Lincoln et al. | 206/63.3 |
| 4,700,833 | 10/1987 | Smith | 206/63.3 X |
| 4,708,241 | 11/1987 | Black | 206/63.3 |
| 4,813,537 | 3/1989 | Okuhara et al. | 206/63.3 |
| 4,896,767 | 1/1990 | Pinheiro | 206/63.3 |
| 4,946,043 | 8/1990 | Roshdy et al. | 206/63.3 |

FOREIGN PATENT DOCUMENTS

| | | |
|---|---|---|
| 3027836 | 3/1982 | Fed. Rep. of Germany . |
| 2331638 | 6/1977 | France . |
| 2455880 | 1/1981 | France ................. 206/63.3 |
| 6504467 | 10/1966 | Netherlands . |
| 7302081 | 8/1973 | Netherlands . |
| 680089 | 10/1952 | United Kingdom . |
| 2148232 | 5/1985 | United Kingdom ............... 206/227 |
| 2161130A | 1/1986 | United Kingdom . |

Primary Examiner—William I. Price
Attorney, Agent, or Firm—Thomas R. Bremer; Peter G. Dilworth; Rocco S. Barrese

[57] ABSTRACT

A package is disclosed for containing a plurality of combined surgical suture devices, particularly of the double armed type having a pledget and used for cardiovascular surgical procedures. A backing panel has a protective cover adhesively affixed to one side and defines a plurality of straight elongated suture tracks for reception of the flexible suture portion therein. An aperture is positioned at each end of each track to facilitate reception of the flexible suture portion into the track and drawing a vacuum therein to assist drawing the flexible suture portion into the track. Preferred embodiments include separate features such as a foam needle park or an end flap configured to support the suture needles beneath tabs. Still another embodiment includes and end flap which defines pockets to receive the needles. A method for packaging such sutures is also disclosed.

52 Claims, 5 Drawing Sheets

PACKAGE FOR NEEDLE SUTURES OR THE LIKE

BACKGROUND OF THE INVENTION

1. Field of the Invention

This invention relates to a package for needle-suture combinations. More particularly, this invention relates to a molded package wherein each suture is double armed and includes a pledget for absorption of body fluids.

2. Description of the Prior Art

Many types of packages for sutures and combined surgical needle-suture devices are known in the art. Generally, a package should be constructed to adequately secure a needle and suture while providing easy withdrawal during use. It is also preferable to minimize the formation of kinks or bends in the suture during storage.

A further objective sought in the design of suture packages is to construct the package in accordance with its intended application. For example, suture packages must often accommodate suture material of high quality generally having a surgical needle at one end, all in a readily dispensable fashion so as to have optimum handling characteristics. Cardiovascular sutures are generally "double armed", i.e. they include a needle at each end of the suture, presenting still additional packaging difficulties. Moreover, in cardiovascular applications differently colored sutures are used for identification purposes.

Generally, the needle-suture devices of a cardiovascular suture package must be secured in spaced relation such that during a critical procedure such as a bypass operation, the surgeon can readily grasp the needles with his forceps and quickly remove the suture from the package without difficulty.

Furthermore, a customary practice in cardiovascular surgery is to attach a pledget to the center of the suture. In such applications, a pledget is used which is a small pad or cushion used to distribute the force of the suture over a greater area of tissue to prevent cutting the relatively delicate tissue with the fine denier suture. In cardiovascular surgery one typical pledget is formed of Teflon brand material, as marketed by DuPont de Nemours, Wilmington, Del. In some instances the pledget is formed of an absorbable material.

A properly configured suture package for such cardiovascular sutures must therefore be constructed in a manner which stores the suture with both needles, as well as the pledget, while allowing the package to be opened and the needle-suture-pledget device to be removed without entanglement of the pledget with the suture or the suture upon itself. The present invention is directed to a suture package wherein a plurality of such needle-suture devices with attached pledgets may be conveniently stored in a single package while maintaining the individuality of each suture with respect to each other.

SUMMARY OF THE INVENTION

A package for surgical suture devices which comprises a backing panel, a protective cover attached to the backing panel and defining a plurality of elongated tracks, each track for receiving at least a portion of a flexible suture, access means to facilitate user access to at least a portion of the flexible suture portion, means at one end portion of the backing panel to permit drawing a vacuum on each elongated track. Preferably, the suture access means is an aperture at one end of each track.

The protective cover preferably is a molded panel, and means is provided to support at least one needle of the suture device. The molded panel has an undulating crosssectional configuration which defines the elongated tracks for reception of the flexible portions of the surgical suture devices. The tracks are each spaced from the next adjacent back by a base portion of the molded panel which is adhesively attached to the backing panel.

The backing panel defines an aperture at a location corresponding to one end track which receives a suture therein. In a preferred embodiment, the means to support at least one needle of each suture device is a strip of foam material adhesively secured to the backing panel adjacent the apertures. The apertures permit the suture device positioned in the corresponding track to extend therethrough to facilitate storing and supporting the needle on the strip of foam material. Preferably, the protective molded panel is molded of clear plastic material which facilitates visual observation of the suture device under each protective track. The apertures are spaced from each other sufficient to permit storage adjacent thereto of an absorbent pledget member.

In another preferred embodiment a second package is attached to the first package and is similar in structure to the first package. The first and second packages are configured such that the respective undulations of each molded protective cover complement the undulations of the other to facilitate foldably connecting the packages together with the protective covers in frictionally engaged relation with each other. Further, an end panel is connected to each backing panel and dimensioned to be folded over the needles to protect the needles. An end tab extends from each end panel and is dimensioned to be folded over the package in a manner to secure the end panels in their folded needle protective positions.

In a preferred embodiment, the package for a combined surgical suture needle device comprises at least one backing panel member, a molded cover panel directly affixed to the backing panel member and having a plurality of straight blister tracks formed along the length of the molded cover panel and defining a relatively wide pocket for receiving a suture therein. A needle park is affixed to a proximal end of the rear side of the backing panel to support needles of the sutures, an extension panel is hingedly attached to the proximal end of the backing panel adjacent to the needle park, the extension panel being foldable over the rear side of the panel to protect the secured needles. A fold-over tab is hingedly attached to one side of the extension panel, the fold-over tab being adapted to fold over the front side of the extension flap to maintain the extension flap against the needles. A plurality of suture receiving ports are disposed along one end portion of the panel and a plurality of vacuum apertures are disposed along the other end portion of the panel, each of the receiving ports being in general alignment with a vacuum aperture and each access aperture, and each vacuum aperture being generally in alignment with a blister track. Each blister track forms an enclosed receptacle for reception of a suture therein. The suture is inserted into a separate compartment formed by the blister track. The molded cover lid is of resilient plastic material and defines at least five blister tracks. The molded cover lid is adhered to the backing panel by a suitable adhesive and the needle park is preferably of styrofoam material. The main panel possesses an extension panel which folds over its edge to protect needles secured to the needle park.

The suture is partially inserted in the blister track which is adapted to be subjected to a vacuum without opening the package. In one embodiment, the extension panel possesses arcuate die cuts forming arcuate shaped tabs to retain the needles and the vacuum apertures are in the form of "+" or "x" shaped slits. In another embodiment, the vacuum apertures are circular.

Generally stated, the invention relates to a package for combined surgical suture devices which comprises, a backing panel, a protective cover attached to the backing panel and defining a plurality of elongated tracks for reception of at least the flexible portion of a needle suture device therein, means located at one end of the backing panel to support at least one needle of the needle suture device, and means at the other end of the backing panel to permit drawing a vacuum on each elongated track. The end panel defines a plurality of pockets each for reception and storing of at least one needle of each suture. Each pocket is located in generally aligned position with the corresponding blister track in which the corresponding suture portion is positioned, and means is provided for supporting at least two needles for each suture by piercingly inserting the pointed end of each needle into the foam material.

The invention also relates to a method for packaging a plurality of suture devices, comprising, taking a backing panel having a plurality of apertures at one end portion for directing a vacuum therethrough, and a plurality of apertures at the other end portion and in general alignment with the first mentioned apertures for reception of at least a portion of a suture device, adhesively attaching a protective cover to the backing panel, the protective cover having a plurality of elongated tracks, each track for reception of at least a portion of a suture device, each track being in general alignment with a respective pair of opposed apertures in the backing panel. The method comprises at least partially inserting a suture device to be packaged into each of the last mentioned apertures and drawing a vacuum through the first mentioned apertures to at least partially assist drawing at least a substantial portion of each suture into the respective elongated track communicating with each of the first mentioned respective apertures. A double package for such sutures is also disclosed whereby combined surgical suture devices of different types or colors may be separately packaged, one type or color in each package.

BRIEF DESCRIPTION OF THE DRAWINGS

Preferred embodiments of the invention are described hereinbelow with reference to the drawings wherein.

DESCRIPTION OF THE PREFERRED EMBODIMENTS

Figure 1:
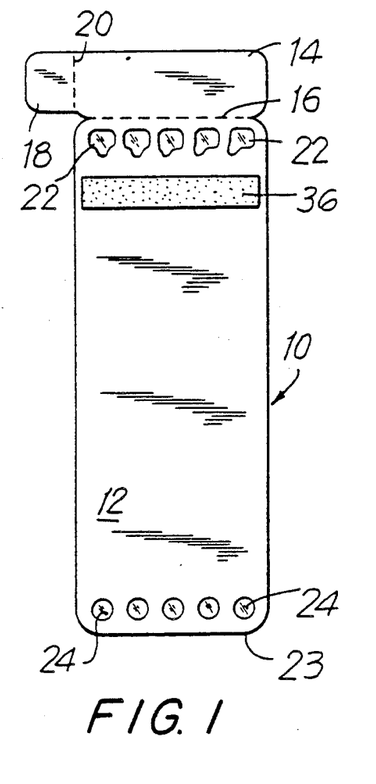
FIG. 1 is a rear plan view of a package constructed according to the present invention.

Referring initially to FIG. 1 the suture package 10 according to the present invention is illustrated. Package 10 includes backing panel 12, end panel 14, defined in part by perforated score line 16, and adhesively backed side tab 18 extending from one side of end panel 14 and defined in part by perforated score line 20. Backing panel 12 has an equal number of suture receiving ports 22 and vacuum apertures 24, respectively disposed at the top and bottom ends of backing panel 12. Each suture receiving port 22 is longitudinally aligned with a corresponding vacuum aperture 24. Needle receiving park 36 is positioned below suture receiving ports 22 for retaining a plurality of curved needles which are connected to the flexible suture material extending through receiving ports 22. Needle receiving park 36 is preferably a strip of styrofoam material which is readily pierced by the needles to retain the needles in position. This material is adhesively attached to backing panel 12.

Figure 2:
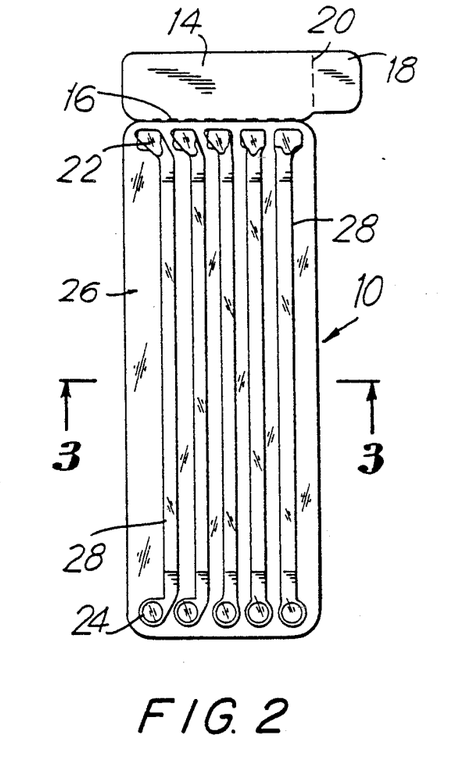
FIG. 2 is a frontal plan view of the package of FIG. 1 illustrating a plurality of blister tracks for receiving the sutures.
Figure 3:
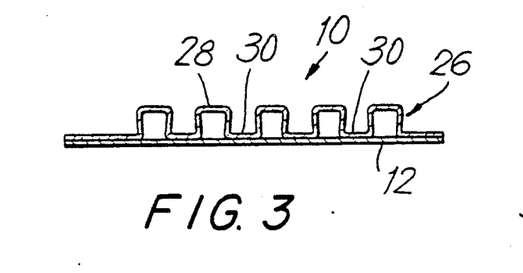
FIG. 3 is an enlarged cross-sectional view taken along lines 3—3 of FIG. 2, illustrating the configuration of the blister tracks.

Referring now to FIG. 2 in conjunction with the cross-section shown in FIG. 3, the front side of suture package 10 is illustrated. Molded blister panel 26 is adhered to the marginal surface of backing panel 12 by a suitable adhesive. Blister panel 26 possesses a plurality of raised blister tracks 28. Each blister track 28 is longitudinally oriented with respect to backing panel 12 and terminates at one end at a suture receiving port 22 and at its other end at a corresponding vacuum aperture 24 to provide communication therebetween. As shown in the cross-sectional view in FIG. 3, the blister tracks are formed in an undulating shape such that each track 28 is separated from the next adjacent tracks by a base 30 which is also adhesively secured to the backing panel 12. Each blister track 28 is dimensioned adequately to accommodate the folded double-armed suture device of FIG. 4.

Figure 4:
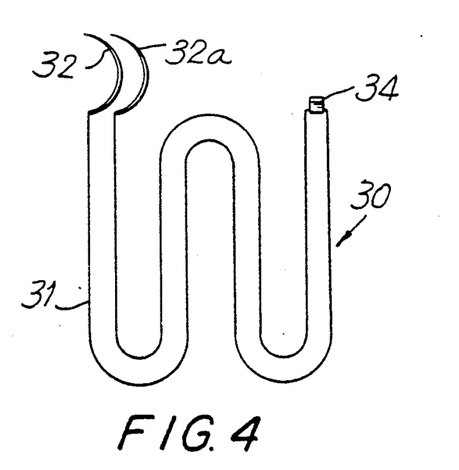
FIG. 4 illustrates a typical double armed needle-suture device including a pledget, folded in the manner shown prior to storage in the package of FIG. 1.

Referring now to FIG. 4, there is illustrated a double armed suture device 30 of the type intended to be loaded into each blister track 28 of suture package 10. The double-armed suture device is specifically folded upon itself in a double loop configuration as shown, with attached arcuate needles, 32 and 32a, and pledget 34 which becomes positioned adjacent the needles as shown when the suture device is folded. This arrangement facilitates loading into the package and easy removal during operating room procedures.

In cardiovascular procedures, pledget 34 is a pad of a non-absorbent material such as Teflon brand material marketed by DuPont de Nemours, Wilmington, Del. The teflon pad is used to assist starting the stitching process by serving as an anchor and by distributing the force of the suture over a large tissue area to prevent cutting the tissue with the fine denier sutures. Curved needles 32, 32a are of the type which are used in cardiovascular surgery and are constructed of 300 or 400 series surgical stainless steel. However other needles, such as straight needles, or absorbable pledgets, may be packaged, depending upon the intended application.

Figure 5:
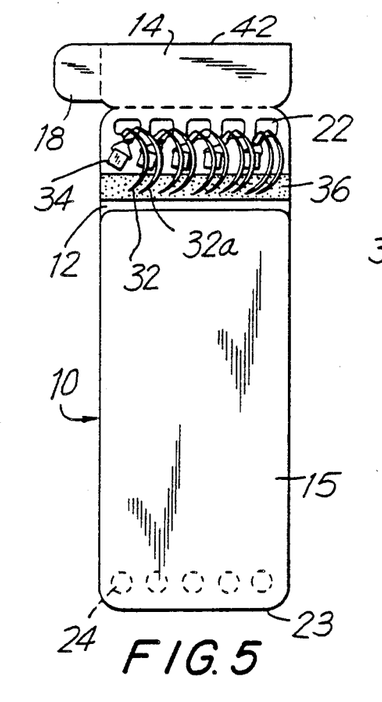
FIG. 5 is a plan view of the rear side of the package of FIG. 1 with one preferred form of needle receiving park provided, and the needles of the type shown in FIG. 4 lodged in the needle receiving park.

A plurality of double-armed sutures 30, as illustrated in FIG. 4, are loaded into suture package 10 by partially inserting the looped portion of suture 31 of double armed suture device 30 into suture receiving ports 22 and applying a vacuum through the appropriate corresponding vacuum aperture 24 to assist in drawing the double-armed suture device into blister track 28 until needles 32 and 32a and pledget 36 are adjacent to suture receiving part 22. Thereafter, the base of needles 32 and 32a may be partially positioned in suture receiving ports 22 as shown in FIG. 5, while the tip sections of needles 32 and 32a are piercingly lodged into needle receiving park 36 to adequately retain the needles to base panel 12 in fixed concentric orientations adjacent the pledgets. Pledget 34 is suspended from suture receiving port 22 adjacent needles 32 and 32a.

It may be appropriate while loading the double-armed suture devices into blister tracks 28 to alternate between differently colored sutures. Protocol for coronary surgery often requires medical personnel to use differently colored sutures during a given procedure, i.e. green and white. The advantages of having the blister tracks 28 of suture package 10 loaded with double-armed suture devices in this manner are self-evident. For example, a white suture in the first blister track 28, followed by a green suture in the next, followed by a white suture, etc. will minimize the possibility of medical personnel selecting an improper double-armed suture device.

Referring again to FIG. 5, after loading the double armed suture devices 30 into blister tracks 28, an adhesively coated cover sheet or label 15 is attached to cover the surface on backing panel 12 which extends from edge 23 to needle receiving park 36. A cover sheet or label 15 conceals vacuum apertures 24 thereby preventing foreign material from entering the suture package. Also, if a double-armed suture device is dislodged in the package, cover sheet 15 will prevent suture 31 or a portion thereof from escaping through vacuum aperture 24. End panel 14 is folded downwardly along score line 16 over needles 32, 32a and the upper portion of the backing panel 12 so as to cover and protect the exposed needles and pledget. End tab 18, which may be coated with an appropriate adhesive, folds over the front side of blister panel 26 and is adhesively attached to blister panel 26 to retain end panel 14 secured against the needles.

Figure 6:
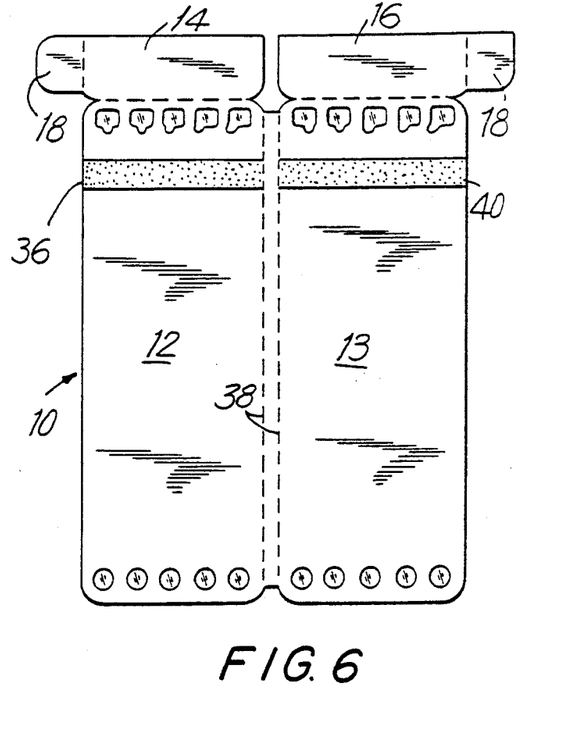
FIG. 6 is a rear plan view of an alternate embodiment of the invention including two panel members foldably connected to each other.
Figure 8:
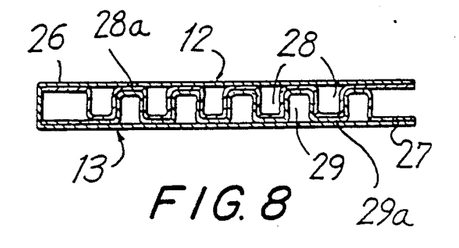
FIG. 8 is a cross-sectional view taken along lines 8—3 of FIG. 7 illustrating the configuration of the blister tracks of the double panel embodiment of FIG. 6 folded and interlocked in the closed position.

Referring now to FIG. 6, an alternative embodiment of the present invention is provided. Suture package 10 includes two backing panels 12, 13 having attached on their front surfaces (not shown in FIG. 6) a blister panel each similar in configuration to the blister panel illustrated in FIG. 2. Backing panels 12 and 13 are foldably connected to each other by double perforate score lines 38 to accommodate the thickness of the package and blister tracks when the package is in the closed position as shown in FIG. 8. Backing panels 12 and 13 can also be separated along double score lines 38 during use, if needed. End panels 14 and 16 are foldably connected to main panels 12, 13 respectively, and folded over the rear sides of each respective panel to cover or partially cover the lodged needles. Needle retainer parks 36 and 40 are shown at different heights with respect to the tops of their respective backing panels 12, 13 to lodge needles of a different size on each panel, if needed. The widths of end tab 18 and 19 are varied in relation to the width of its respective end panel to adequately secure each end panel (14, 16) to its respective backing panel.

Figure 7:
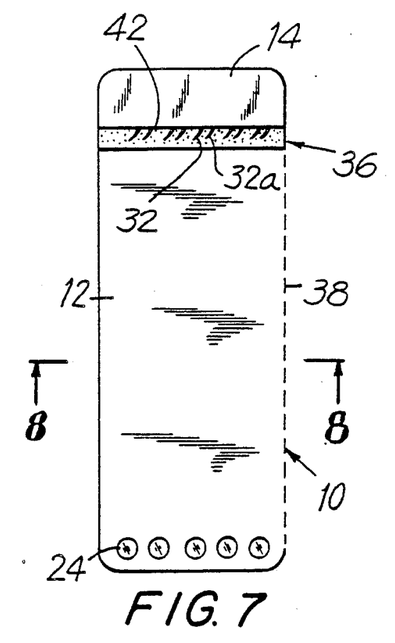
FIG. 7 is a plan view of the package of FIG. 6 in the closed position.

The two panel embodiment of FIG. 6 is secured in the closed position of the package as illustrated in FIG. 7 by loading the double-armed suture devices 30 into the blister tracks. It may be preferable to load backing panel 12 with one colored suture (i.e., green) and load backing panel 13 with another colored suture (i.e., white) to facilitate operating room procedures as previously mentioned. End panels 14 and 16 are folded over backing panels 12 and 13, respectively to rest against the lodged needles. Thereafter end tabs 18 and 19 are adhesively attached to their respective blister panels to fully secure end panels 14 and 16 respectively, against the attached needles. Alternatively, the end tabs 18 and 19 may be provided without adhesive backing and dimensioned of length sufficient to frictionally engage them between the panels when the package is folded.

As shown in FIG. 8, blister panels 26 and 27 of backing panels 12, 13, respectively, are then folded towards their front sides along double score line 38 so that the blister panels meet. As can be seen, each blister track 28 of blister panel 26 is in corresponding alignment with base 29a of blister panel 27. In the same respect, each blister track 29 of blister panel 27 aligns with base 28a of blister panel 26. The two panels are then secured to each other by snapping them together such that the tracks 28 of blister panel 26 interlock by friction with the tracks 29 of adjacent blister panel 27. The tracks 28 and 29' are appropriately configured to adequately maintain the panels in the closed position. Thus, a sufficient force is necessary to pull the panels apart.

Figure 9:
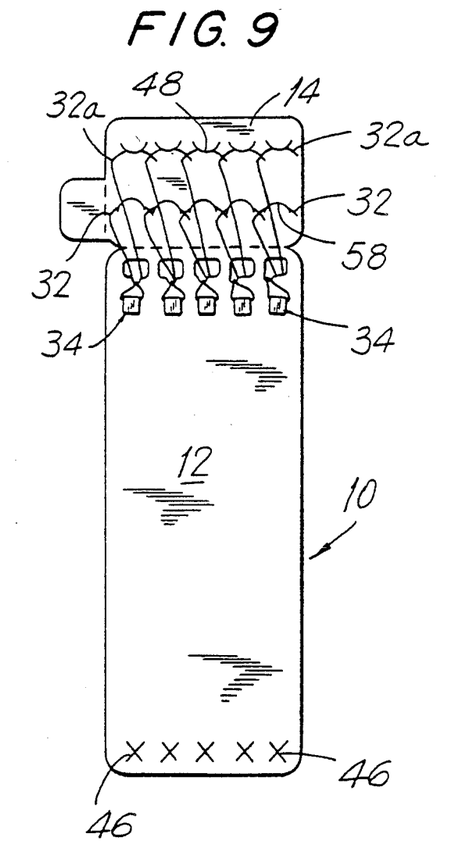
FIG. 9 is a plan view of another embodiment of the package of FIG. 1, with a plurality of cross-slits to permit evacuation of the package and providing arcuate slots to secure the needles in position.
Figure 10:
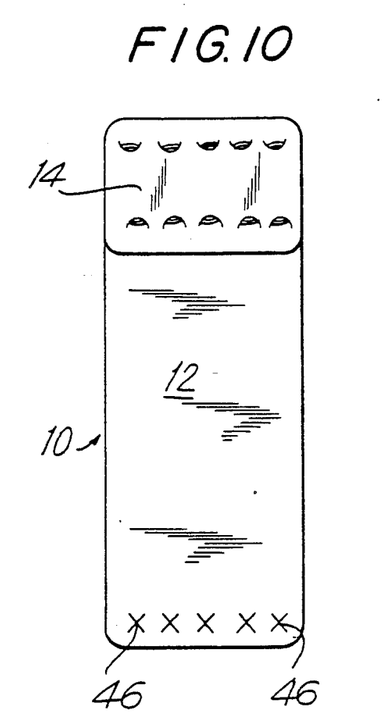
FIG. 10 is a plan view of the package of FIG. 9 in the fully closed position illustrating alternative vacuum drawing apertures in the form of "x" slits.

Referring now to FIGS. 9 and 10, there is illustrated alternative embodiments to end panel 14, needle receiving park 36 and vacuum apertures 24 of the embodiment illustrated in FIGS. 1, 2 and 5. Specifically, end panel 14 of FIG. 9 possesses two rows of a plurality of arcuate shaped slits, which define corresponding arcuate tabs 48 and 50, as shown in the upper and lower halves of end panel 14. Arcuate tabs 48 and 50 are dimensioned, oriented and positioned to be lifted to receive and adequately retain the needles thereunder as shown. Each arcuate tab 48 in the upper row is longitudinally aligned with a corresponding tab 50 in the lower row for securing needles 32 and 32a, respectively, of the double-armed suture device of FIG. 4. Furthermore, arcuate tabs 48 of the upper row as well as arcuate tabs 50 of the lower row are spaced sufficiently to prevent entanglement with neighboring double-armed suture devices. As can be seen, arcuate tabs 48 and 50 also face in opposite directions to facilitate positioning needles 32, 32a as shown for grasping the needles with forceps to provide easy withdrawal during use.

End panel 14 folds onto backing panel 12 and is secured by adhesively adhering end tab 18 to the blister panel. It will be appreciated that end panel 14 does not fold in half over its score line as illustrated in the embodiment of FIGS. 1, 2 and 5, but, remains in the fully unfolded condition when secured.

Another feature of the embodiment shown is the vacuum slits 46 which replace the vacuum apertures of the embodiment of FIG. 1. Vacuum slits 46 are configured in an "x-shape", and, unlike the vacuum apertures 24 of FIG. 1 which are completely open, remain in a relatively closed position during suture storage thereby eliminating the need for attaching a cover sheet to the backing panel to conceal vacuum holes 24 and to protect the sutures from foreign matter. Depending upon individual needs and preferences any of the vacuum apertures may be used in each embodiment. In other respects, the embodiment shown in FIGS. 9 and 10 is essentially the same as the previously described embodiment. Vacuum slit 46 is adapted to open sufficient to draw a vacuum therethrough.

Figure 11:
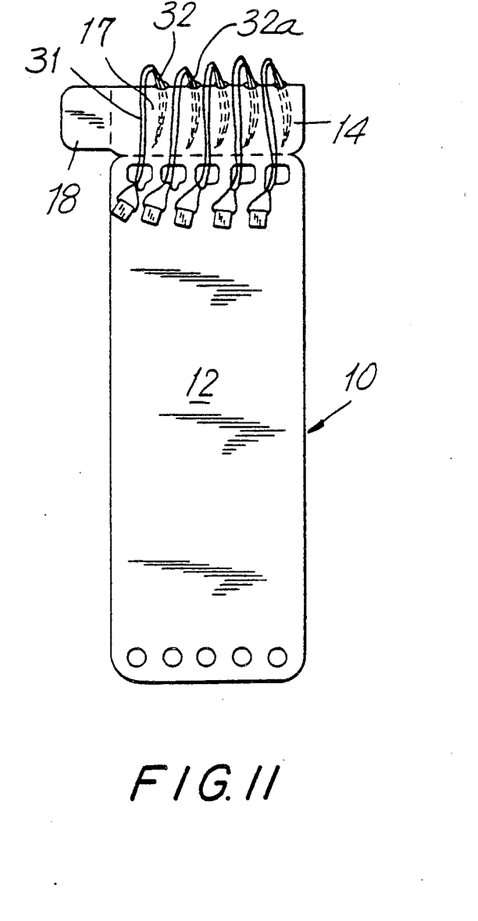
FIG. 11 is a rear view of an alternative embodiment of the invention in which an end flap is provided with a plurality of pockets to receive and support the needles of the sutures.
Figure 12:
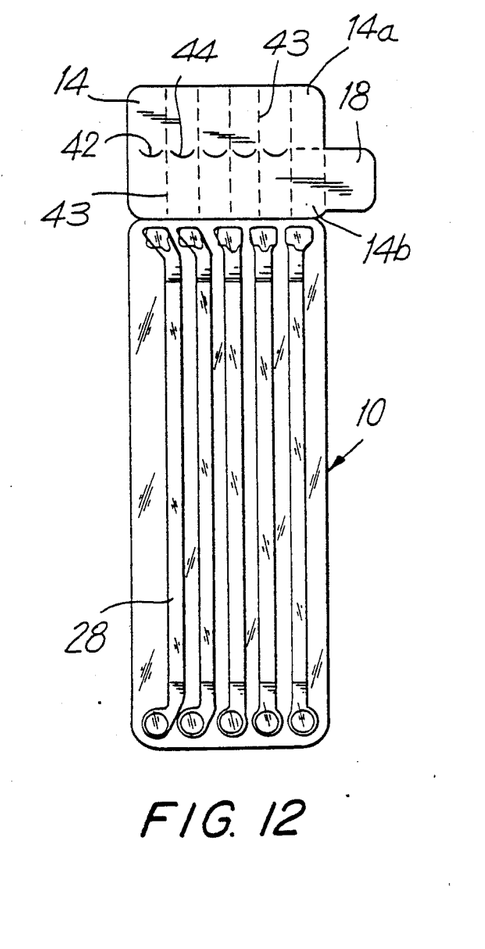
FIG. 12 is a view of the front side of the package of FIG. 11 prior to folding the end flap in half to form the needle pockets with vacuum apertures in the form of "+" slits.

Referring to FIGS. 11 and 12, there is shown an alternative embodiment of the package, formed by the upper panel as shown in FIG. 12. In this embodiment the panel 14 is foldable along the line 42 as shown in FIG. 12, defined by a series of arcuate cuts 44 and includes adhesive backing along dotted lines 43. When upper half section 14a is folded downwardly onto lower half section 14b a series of pockets 15 are formed between dotted lines 43 which identify adhesive lines. The pockets receive and support the needles 32 and 32a as shown in FIG. 11 with arcuate cuts 44 providing an aperture for reception of the needle, thereby avoiding the need for the needle park 36 shown in the embodiment of FIG. 1 End panel 14 is then folded downwardly over backing panel 12 and may be adhesively backed to secure it in position. End tab 48 may also be adhesively backed and folded over the front side to retain the end panel 14 in the folded, or "needle protective" position.

Figure 13:
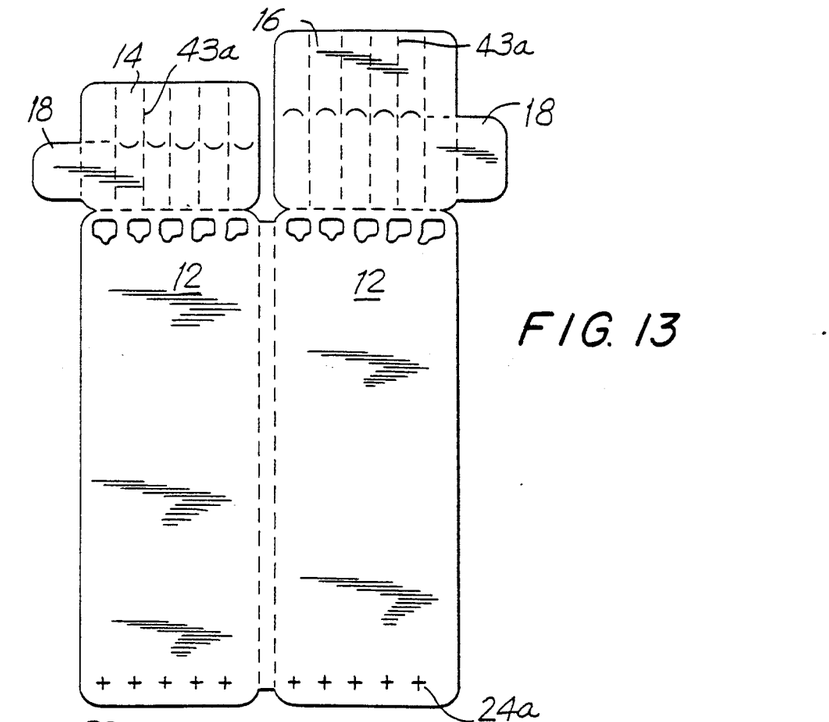
FIG. 13 is a rear view of still another alternative embodiment of the invention illustrating a pair of separable panels of the type shown in FIG. 11 in an arrangement similar to the embodiment of FIG. 6.
Figure 14:
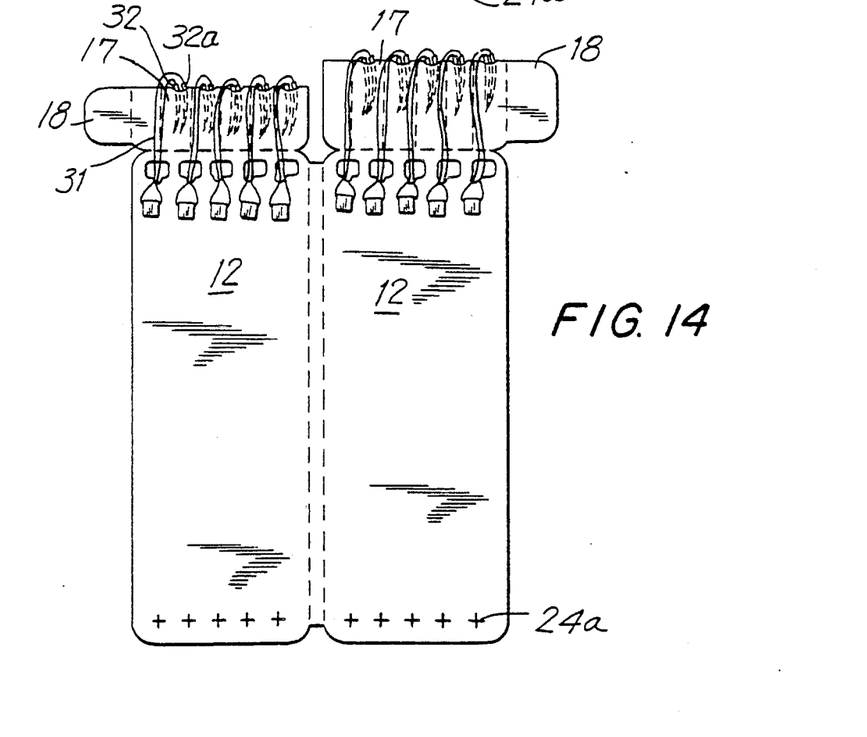
FIG. 14 is a view of the front side of the embodiment of FIG. 13 with the needle pockets formed and supporting the needles therein.

Referring to FIG. 13, there is shown an embodiment similar to the package of FIG. 11 but in the form of a double pack similar to the embodiment of FIG. 6, with "+" shaped slits at the bottom to permit drawing a vacuum. The end flaps 14 and 16 are of different heights and include self stick adhesive along dotted lines 43a such that when folded downwardly, as shown, the flaps form needle pockets as shown in FIG. 14. The height of the right side end panel 16 is greater than panel 14 to facilitate ready identification of the different colored sutures, one color such as green, being on the right side package, and the other color, such as white, being on the left side package. The embodiment of FIGS. 11-14 advantageously expose the needle shanks upon opening the package to allow 360 degrees access for gripping and removing the needles and flexible suture portions.

What is claimed is:

1. A package for surgical suture devices which comprises:
   a) a backing panel;
   b) a protective cover attached to said backing panel and defining a plurality of elongated tracks, each track for receiving at least a portion of a flexible suture;
   c) access means at one end portion of said tracks and communicating therewith to facilitate insertion and removal at least a portion of each said flexible suture portion; and
   d) aperture means extending through said backing panel and spaced from said access means, said aperture means being positioned to permit drawing a vacuum on each elongated track.

2. The package according to claim 1 wherein said protective cover is a molded panel.

3. The package according to claim 2 wherein means is provided to support at least one needle of said suture device.

4. The package according to claim 3 wherein said molded panel has an undulating cross-sectional configuration which defines said elongated tracks for reception of the flexible portions of the surgical suture devices.

5. The package according to claim 4 wherein said tracks are each spaced from the next adjacent track by a base portion of said molded panel.

6. The package according to claim 5 wherein said molded panel is adhesively attached to said backing panel.

7. The package according to claim 6 wherein said suture access means is an aperture at a location corresponding to one end of each said tracks which receive a suture therein.

8. The package according to claim 7 wherein said means to support said at least one needle of each suture device is a strip of foam material adhesively secured to said backing panel adjacent said apertures, said apertures permitting the suture device positioned in the corresponding track to extend therethrough to facilitate storing and supporting said needle on said strip of foam material.

9. The package according to claim 8 wherein said protective molded panel is molded of clear plastic material which facilitates visual observation of the suture device under each protective track.

10. The package according to claim 9 wherein said apertures are spaced from each other sufficient to permit storage adjacent thereto of an absorbent pledget member.

11. The package according to claim 10 wherein a second package is attached to said first package, said second package being similar in structure to said first package and connected by at least one perforated tear line.

12. The package according to claim 11 wherein said first and second packages are configured such that the respective undulations of each molded protective cover complement the undulations of the other to facilitate foldably connecting the packages together with said protective covers in frictionally engaged relation with each other.

13. The package for according to claim 11 further comprising an end panel connected to each backing panel and dimensioned to be folded over said needles to protect said needles.

14. The package for according to claim 13 further comprising an end tab from each said end panel and dimensioned to be folded over the package in a manner to secure said end panels in their folded needle protective positions.

15. A package for a combined surgical suture needle device which comprises:
a) at least one backing panel member;
b) a molded cover panel directly affixed to a first side of said backing panel member and having a plurality of straight blister tracks formed along the length of said molded cover panel and defining a pocket for receiving a suture therein;
c) a needle park affixed to a first end portion of a second side of said backing panel to support needles of said sutures;
d) an extension panel hingedly attached to a first end of said backing panel adjacent to said needle park, said extension panel being foldable over the second side of said backing panel to protect the secured needles;
e) a fold-over tab hingedly attached to being adapted to fold of said extension panel, said fold-over tab being adapted to fold over a front side of said molded cover panel to maintain said extension panel in folded position against said needles; and
f) a plurality of suture receiving ports disposed along said first end portion of said backing panel and a plurality of vacuum apertures disposed along a second end portion of said backing panel, each said receiving ports being in general alignment with a vacuum aperture, and each said vacuum aperture being generally in alignment with a blister track.

16. The package according to claim 15 wherein said molded cover panel is of resilient plastic material.

17. The package according to claim 16 wherein each said blister track forms an enclosed receptacle for reception of a suture therein.

18. The package according to claim 17 wherein a suture is at least partially inserted into a separate compartment formed by said blister track.

19. The package according to claim 18 wherein said molded cover panel defines at least five blister tracks.

20. The package according to claim 19 wherein said molded cover panel is adhered to said panel by adhesive.

21. The package according to claim 20 wherein said needle park is of styrofoam material.

22. The package according to claim 21 wherein said suture is inserted in said blister track and said blister track is adapted to be subjected to a vacuum without opening the package.

23. The package according to claim 22 wherein said extension panel possesses arcuate die cuts forming arcuate shaped tabs to retain at least portions of said needles thereunder.

24. The package according to claim 23 wherein said vacuum aperture are defined by at least one of a "+" shaped slit end "x" shaped slit.

25. The package according to claim 23 wherein said vacuum apertures are circular.

26. A package for combined surgical suture devices which comprises:
a) a backing panel;
b) a protective cover attached to said backing panel and defining a plurality of elongated tracks for reception of at least the flexible portion of a needle suture device therein;
c) means located at one end of said backing panel to support at least one needle of said needle suture devices;
d) means communicating with each elongated track to facilitate insertion and removal of at least a portion of each surgical suture device; and
e) aperture means at the other end of said backing panel and extending through said backing panel and positioned to permit drawing a vacuum on each elongated track.

27. The package according to claim 26 wherein said means for supporting said at least one needle comprises an end panel connected to said backing panel and defining a plurality of adjacent pockets each for reception and storing of at least one needle of each suture.

28. The package according to claim 27 wherein each pocket is located in generally aligned position with the corresponding elongated track in which the corresponding suture portion is positioned.

29. The package according to claim 28 wherein said means for supporting at least one needle is a strip of foam material dimensioned, configured and positioned to support at least two needles for each suture by piercingly inserting the pointed end of each needle into said foam material.

30. The package according to claim 29 wherein said backing panel includes a vacuum aperture defined by at least one of a circular aperture, "+" shaped cut and "x" shaped cut each at a location in alignment with the corresponding elongated track.

31. The package according to claim 30 wherein at least a second package is removably attached to said first package, said second package having a plurality of elongated tracks, said second package including an extension panel defining a plurality of pockets corresponding to said elongated tracks, said extension panel of said first package being of height different from said extension panel of said second package to facilitate ready identification of the corresponding suture in each package as viewed by the different heights of the needles positioned in said pockets.

32. The package according to claim 31 wherein the sutures positioned in said first package are of different color than the sutures in said second package.

33. A package for combined needle suture devices which comprises:
a) a backing panel;
b) a molded cover panel attached to said backing panel and having an undulating cross-sectional configuration which defines a plurality of straight elongated tracks, each track for reception of at least the flexible portion of a double armed suture device;
c) means at one end of said tracks for supporting at least one needle of each suture device;
d) aperture means at the other end of said tracks, said aperture means extending through said backing panel and positioned to permit drawing a vacuum within each track to at least partially assist drawing at least the flexible portion of a suture device therein;
e) means to facilitate insertion and removal of at least a portion of each suture device; and
f) a second backing panel and molded cover panel substantially similar to said first backing panel and molded cover panel and attached thereto along at least one hinge line whereby combined surgical suture devices of the same color or combined surgical suture devices of different types or colors may be selectively drawn into said tracks for storage until used.

34. The package according to claim 33 wherein said needle support means is adapted to support a plurality of needles.

35. The package according to claim 34 wherein said means for supporting needles comprises a foam strip attached to each backing panel on the side opposite said molded cover panel for pierced reception of a needle of a suture.

36. The package according to claim 33, wherein said means for supporting suture needles comprises an end flap connected to each said backing panel and defining a plurality of adjacent pockets for reception of said needles therein.

37. The package according to claim 36 wherein said end flap connected to one of said backing panels is of height greater than said end flap connected to said other backing panel such that the needles received in said first end flap are at a different height than said needles received in said other end flap.

38. The package according to claim 37 wherein said end flap is formed of a first layer of material having adhesive strips spaced from each other such that when half of said end flap is folded over the remaining half thereof, the two halves define adjacent pockets for needles, said pockets being spaced by adhesively attached portions of said half flaps.

39. The package according to claim 38 wherein said end flaps contain a plurality of arcuate cuts positioned generally vertically thereof, the material surrounding said cuts being such as to form a needle reception opening for each pocket when half of said first flap is folded and adhesively attached to said other half end flap to form said pockets.

40. The package according to claim 33 wherein said means to facilitate insertion and removal of a suture portion is an aperture in said backing panel at one end portion corresponding to each track.

41. The package according to claim 33 wherein said hinge line is a perforated tear line which permits selective separation of said backing panels.

42. A method for packaging a plurality of suture devices, comprising:
a) taking a backing panel having a plurality of apertures at a first end portion for reception of at least a portion of a suture device, and a plurality of apertures at a second end portion and in general alignment with said first mentioned apertures for directing a vacuum therethrough;
b) adhesively attaching a protective cover to a first side of said backing panel, said protective cover having a plurality of elongated tracks, each track for reception of at least a portion of a suture device, and each track being in general alignment with a respective pair of opposed apertures in said backing panel;
c) at least partially inserting a suture device to be packaged into each said first mentioned apertures; and
d) drawing a vacuum through said last mentioned apertures to at least partially assist in drawing at least a substantial portion of each suture into the respective elongated track communicating with each said last mentioned respective apertures.

43. A package for surgical suture devices which comprises:
a) a backing panel;
b) a protective cover attached to said backing panel and defining a plurality of elongated tracks, each track for receiving at least a portion of a flexible suture;
c) access means at one end portion of each track and communicating therewith to facilitate insertion and removal of at least a portion of each said flexible suture portion; and
d) aperture means extending through said backing panel and located at the opposite end portion of said tracks to permit drawing a vacuum on each elongated track.

44. A method for packaging a plurality of suture devices, comprising:
a) taking a backing panel having a plurality of apertures at a first end portion for reception of at least a portion of a suture device, and a plurality of apertures at a second end portion and in general alignment with said first mentioned apertures for directing a vacuum therethrough;
b) adhesively attaching a protective cover to a first side of said backing panel, said protective cover having a plurality of elongated tracks, each track for reception of at least a portion of a suture device, and each track being in general alignment with a respective pair of opposed apertures in said backing panel;
c) at least partially inserting a suture device to be packaged into each said first mentioned apertures;
d) drawing a vacuum through said last mentioned apertures to at least partially assist in drawing at least a substantial portion of each suture into the respective elongated track communicating with each said last mentioned respective apertures; and
e) securing at least one needle of each said suture devices to a needle park, said needle park being adhesively secured to said first end portion of said backing panel adjacent said first mentioned apertures.

45. The method according to claim 34, further comprising the step of adhering a cover sheet to a second side of said backing panel to conceal said last mentioned apertures.

46. The method according to claim 43, wherein said needle park is a strip of foam material.

47. A method for packaging combined needle suture devices in a package having a first backing panel attached along at least one hinge line to a second backing panel, each said backing panels respectively having a plurality of apertures at a first end portion and a plurality of apertures at a second end portion in general alignment with said apertures at said first end portion, each backing panel having an extension panel attached to a first end of said backing panels, comprising:
a) adhesively attaching a first and second protective cover to each said first and second backing panels, respectively, each said protective covers having a plurality of elongated tracks, each track configured and dimensioned for reception of at least a portion of a suture device and for interlocking engagement with the tracks of the other cover, each track further being in general alignment with a respective pair of opposed apertures in each of said backing panels;
b) at least partially inserting a suture device in each aperture at said first end portion of said backing panels, drawing a vacuum through each of said apertures at said second end portion of said backing panels to at least partially assist drawing at least a substantial portion of each suture into the respective elongated track communicating with each said apertures at said second end portion;

c) securing at least one needle of said suture devices to a needle park adhesively secured to each said first end portions of said backing panels;

d) folding each said extension panel over said needles to retain the needles against each of said backing panels; and e) folding said first protective cover onto said second protective cover such that said elongated tracks of said first protective cover frictionally interlock with said second panel cover to maintain a closed position of the package.

48. A package for surgical suture devices which comprises:

a) a backing panel;

b) a molded protective cover panel adhesively attached to said backing panel and having an undulating cross-sectional configuration which defines a plurality of elongated tracks for reception of the flexible portions of the surgical suture devices, each track being spaced from the next adjacent track by a base portion of said molded panel, each said track being spaced from the next adjacent track by a base portion of said molded panel;

c) suture access means to facilitate user access to at least a portion of each said flexible suture portion, said suture access means being an aperture in said backing panel at a location corresponding to one end of each said tracks which receive at least a portion of a suture therein;

d) means at one end portion of said backing panel to permit drawing a vacuum on each elongated track;

e) means to support at least one needle of a suture device; and f) a strip of foam material adhesively secured to said backing panel adjacent said suture access means, said apertures permitting the suture device positioned in the corresponding track to extend therethrough to facilitate storing and supporting said needle on said strip of foam material.

49. A package for combined needle suture devices which comprises:

a) a backing panel;

b) a molded cover panel attached to said backing panel and having an undulating cross-sectional configuration which defines a plurality of straight elongated tracks, each track for reception of at least the flexible portion of a double armed suture device;

c) a foam strip attached to said backing panel on the side opposite said molded cover panel for pierced reception of a needle of a suture;

d) means at the other end of said tracks to permit drawing a vacuum within each track to at least partially assist drawing at least the flexible portion of a suture device therein;

e) means to provide user access to at least a portion of each suture device; and f) a second backing panel and molded cover panel substantially similar to said first backing panel and molded cover panel and attached thereto along at least one hinge line whereby combined surgical suture devices of the same color or combined surgical suture devices of different types or colors may be selectively drawn into said tracks for storage.

50. A package for combined needle suture devices which comprises:

a) a backing panel;

b) a molded cover panel attached to said backing panel and having an undulating cross-sectional configuration which defines a plurality of straight elongated tracks, each track for reception of at least the flexible portion of a double armed suture device;

c) means at one end of said tracks for supporting suture needles comprising an end flap connected to said backing panel and defining a plurality of adjacent pockets for reception of said needles therein;

d) means at the other end of said tracks to permit drawing a vacuum within each track to at least partially assist drawing at least the flexible portion of a suture device therein;

e) means to provide user access to at least a portion of each suture device; and f) a second backing panel and molded cover panel substantially similar to said first backing panel and molded cover panel and attached thereto along at least one hinge line whereby combined surgical suture devices of the same color or combined surgical suture devices of different types or colors may be selectively drawn into said tracks for storage.

51. A package for combined needle suture devices which comprises:

a) a backing panel;

b) a molded cover panel attached to said backing panel and having an undulating cross-sectional configuration which defines a plurality of straight elongated tracks, each track for reception of at leas the flexible portion of a double armed suture device;

c) means at one end of said tracks for supporting at least one needle of each suture device;

d) means at the other end of said tracks to permit drawing a vacuum within each track to at least partially assist drawing at least the flexible portion of a suture device therein;

e) suture access means in the form of an aperture in said backing panel at one end portion corresponding to each track; and f) a second backing panel and molded cover panel substantially similar to said first backing panel and molded cover panel and attached thereto along at least one hinge line whereby combined surgical suture devices of the same color or combined surgical suture devices of different types or colors may be selectively draw into said tracks for storage.

52. A package for combined needle suture devices which comprises:

a) a backing panel;

b) a molded cover panel attached to said backing panel and having an undulated cross-sectional configuration which defines a plurality of straight elongated tracks, each track for reception of at least the flexible portion of a double armed suture device;

c) means at one end of said tracks for supporting at least one needle of each suture device;

d) means at the other end of said tracks to permit drawing a vacuum within each track to at least partially assist drawing at least the flexible portion of a suture device therein;

e) means to provide user access to at least a portion of each suture device; and f) a second backing panel and molded cover panel substantially similar to said first backing panel and molded cover panel and attached thereto along at least one perforated tear line which permits selective separation of said backing panels, whereby combined surgical suture device of different types or colors may be selectively drawn into said tracks for storage.

* * * * *